(12) United States Patent
Ando

(10) Patent No.: US 10,258,263 B2
(45) Date of Patent: Apr. 16, 2019

(54) BIOLOGICAL INFORMATION MEASUREMENT CARTRIDGE AND MEASUREMENT DEVICE USING SAME

(71) Applicant: PHC HOLDINGS CORPORATION, Minato-ku, Tokyo (JP)

(72) Inventor: Hiroshi Ando, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 863 days.

(21) Appl. No.: 14/355,575

(22) PCT Filed: Oct. 29, 2012

(86) PCT No.: PCT/JP2012/006905
§ 371 (c)(1),
(2) Date: Apr. 30, 2014

(87) PCT Pub. No.: WO2013/069223
PCT Pub. Date: May 16, 2013

(65) Prior Publication Data
US 2014/0303467 A1    Oct. 9, 2014

(30) Foreign Application Priority Data

Nov. 8, 2011  (JP) .................................. 2011-244238
Jul. 30, 2012  (JP) .................................. 2012-167973

(51) Int. Cl.
*A61B 5/15*       (2006.01)
*A61B 5/145*      (2006.01)
(Continued)

(52) U.S. Cl.
CPC .......... *A61B 5/14532* (2013.01); *A61B 5/157* (2013.01); *A61B 5/1519* (2013.01);
(Continued)

(58) Field of Classification Search
None
See application file for complete search history.

(56) References Cited

U.S. PATENT DOCUMENTS 5,357,971 A * 10/1994 Sheehan ............. A61B 5/0836
128/205.12
5,797,879 A * 8/1998 DeCampli ........... A61B 5/6862
604/93.01
(Continued)

FOREIGN PATENT DOCUMENTS

JP    H04-194660 A    7/1992
JP    2004-329248 A    11/2004
(Continued)

OTHER PUBLICATIONS

International Search Report of Int'l Appln. No. PCT/JP2012/006905 dated Nov. 20, 2012.

*Primary Examiner* — Matthew Kremer
(74) *Attorney, Agent, or Firm* — Wenderoth, Lind & Ponack, L.L.P.

(57) ABSTRACT

A rectangular parallelepiped-shaped cartridge main body having a protective cap removably attached to a first end side thereof has a puncture needle retainer that retains a puncture needle provided at the back of a puncture opening provided on the first end side of the cartridge main body such that the puncture needle is slidable toward the puncture opening. Furthermore, a sensor unit having a depositing opening is provided on the first end side of the cartridge main body. The sensor unit has an introduction promoting hole that communicates with an introduction channel communicating with the depositing opening and that opens to the surface of the cartridge main body. The protective cap is provided with a puncture needle protector that covers the puncture needle, a (Continued)

sensor protector that covers the depositing opening of the sensor unit, and a sensor protector that covers the introduction promoting hole.

10 Claims, 9 Drawing Sheets

(51) Int. Cl.
    *A61B 5/151*     (2006.01)
    *A61B 5/157*     (2006.01)

(52) U.S. Cl.
    CPC .... *A61B 5/150022* (2013.01); *A61B 5/15113* (2013.01); *A61B 5/15142* (2013.01); *A61B 5/15194* (2013.01); *A61B 5/150267* (2013.01); *A61B 5/150358* (2013.01); *A61B 5/150412* (2013.01); *A61B 5/150503* (2013.01); *A61B 5/150717* (2013.01)

(56) References Cited

U.S. PATENT DOCUMENTS

| | | | | |
|---|---|---|---|---|
| 6,036,924 A | * | 3/2000 | Simons | A61B 5/150022 |
| | | | | 600/583 |
| 7,771,368 B2 | * | 8/2010 | Nakamura | A61B 5/14532 |
| | | | | 600/583 |
| 7,815,579 B2 | | 10/2010 | Roe | |
| 2002/0143272 A1 | * | 10/2002 | Crawford | B01L 3/502715 |
| | | | | 600/573 |
| 2006/0129172 A1 | * | 6/2006 | Crossman | A61B 5/15142 |
| | | | | 606/181 |
| 2006/0200045 A1 | | 9/2006 | Roe | |
| 2008/0319345 A1 | * | 12/2008 | Swenson | A61B 5/15003 |
| | | | | 600/576 |
| 2009/0198265 A1 | * | 8/2009 | Ono | A61B 5/15186 |
| | | | | 606/182 |
| 2010/0069792 A1 | * | 3/2010 | Fujimura | A61B 5/14532 |
| | | | | 600/583 |
| 2010/0168615 A1 | * | 7/2010 | Amano | A61B 5/150022 |
| | | | | 600/583 |
| 2010/0210970 A1 | * | 8/2010 | Horikawa | A61B 5/150022 |
| | | | | 600/583 |
| 2011/0000168 A1 | | 1/2011 | Roe | |
| 2011/0009775 A1 | | 1/2011 | Roe | |

FOREIGN PATENT DOCUMENTS

| | | |
|---|---|---|
| JP | 2008-531155 A | 8/2008 |
| JP | 4443142 B2 | 3/2010 |
| WO | 2006-092281 A2 | 9/2006 |

* cited by examiner

BIOLOGICAL INFORMATION MEASUREMENT CARTRIDGE AND MEASUREMENT DEVICE USING SAME

PRIORITY

This application claims priority under 35 U.S.C. § 120 and 35 U.S.C. § 365 to International Application PCT/JP2012/006905, with an international filing date of Oct. 29, 2012, which claims priority to Japanese Patent Application No. 2011-244238 filed on Nov. 8, 2011 and Japanese Patent Application No. 2012-167973 filed on Jul. 30, 2012. The entire disclosures of International Application PCT/JP2012/006905, to Japanese Patent Application No. 2011-244238, and Japanese Patent Application No. 2012-167973 are hereby incorporated herein by reference.

TECHNICAL FIELD

The present invention relates to a biological information measurement cartridge for use in measurement of blood glucose level, for example, and a measurement device using the biological information measurement cartridge.

BACKGROUND

Conventional biological information measurement cartridges have configurations as described below.

Specifically, a conventional biological information measurement cartridge includes a cartridge main body having a puncture opening on a first end side thereof, a puncture needle provided at the back of the puncture opening, and a sensor unit having a depositing opening on the first end side of the cartridge main body.

The biological information measurement cartridge is adapted so that during storage, a plurality of biological information measurement cartridges are placed and stored in a storage container (see Patent Literature 1: JP 2008-531155T, for example).

According to the above conventional example, during storage of the biological information measurement cartridge, a plurality of biological information measurement cartridges are placed and stored in the storage container. For this reason, there are cases where when a single biological information measurement cartridge is taken out from this storage container in order to measure a biological sample, the lid of the storage container may be inadvertently left open.

In such cases, the sensor units of the other biological information measurement cartridges in the storage container will be exposed to air, resulting in a problem that those cartridges can no longer be used.

SUMMARY

The invention includes a cartridge main body having a rectangular parallelepiped shape and including a puncture opening on a first end side thereof, and a protective cap removably attached to the first end side of the cartridge main body. The cartridge main body includes a puncture needle that is provided at a back of the puncture opening, a puncture needle retainer that retains the puncture needle such that the puncture needle is slidable toward the puncture opening, and a sensor unit including a depositing opening on the first end side of the cartridge main body. The sensor unit includes an introduction channel communicating with the depositing opening, and an introduction promoting hole that communicates with the introduction channel and opens to the surface of the cartridge main body. Furthermore, the protective cap is provided with a puncture needle protector that covers the puncture needle, a first sensor protector that covers the depositing opening of the sensor unit, and a second sensor protector that covers the introduction promoting hole of the sensor unit.

As described above, according to the biological information measurement cartridge of the invention, since the protective cap is provided with the puncture needle protector and as well as the first sensor protector and the second sensor protector for the depositing opening and the introduction promoting hole of the sensor unit, exposure of the sensor unit is prevented.

With the above configuration, every biological information measurement cartridge according to the invention that is stored in a storage container is configured to prevent exposure of the sensor unit, and thus proper measurement can be made every time.

DETAILED DESCRIPTION

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

First Embodiment

A first embodiment of the invention applied to a biological information measurement cartridge for use in measurement of blood glucose level, for example, will be described using the accompanying drawings.

Figure 1:
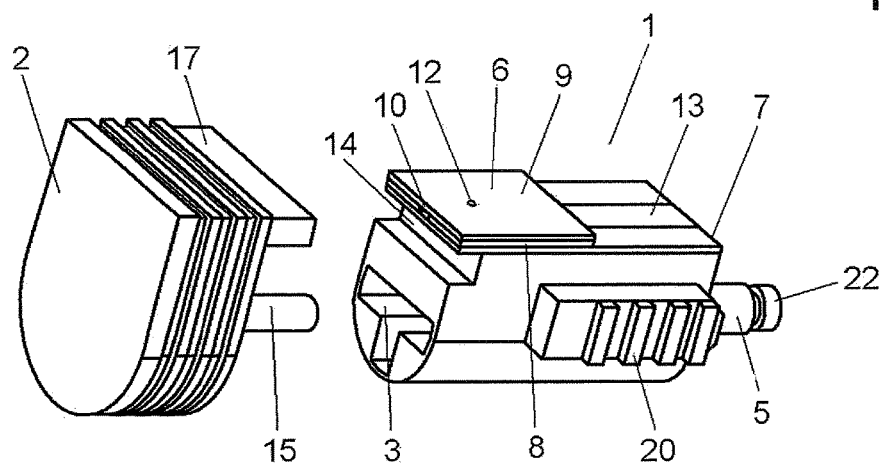
FIG. 1 is an exploded perspective view of a biological information measurement cartridge according to a first embodiment of the invention.
Figure 2:
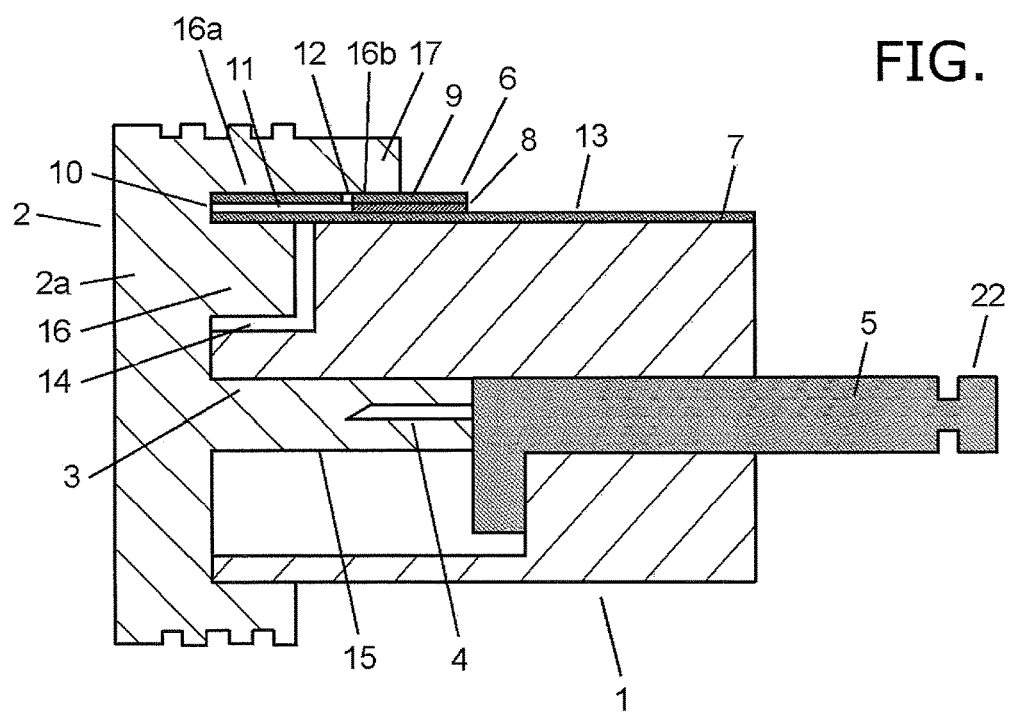
FIG. 2 is a cross-sectional view of the biological information measurement cartridge according to the first embodiment of the invention.
Figure 3:
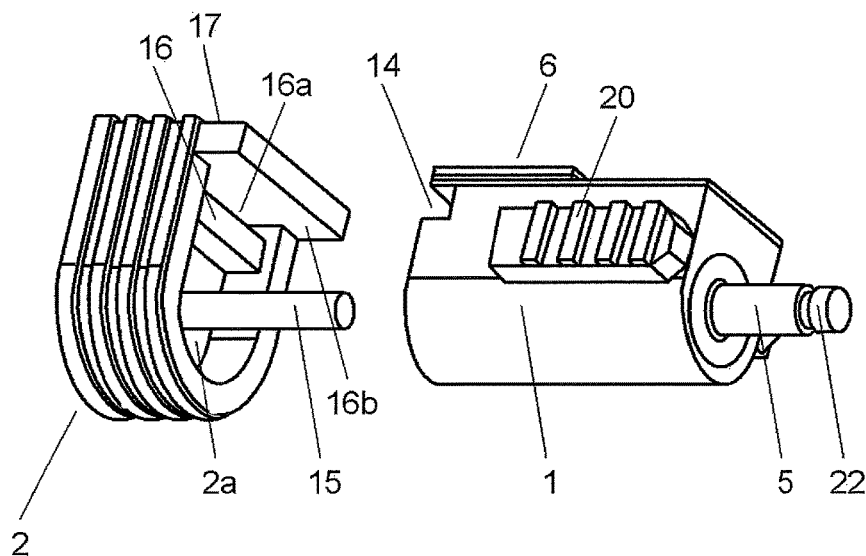
FIG. 3 is an exploded perspective view of the biological information measurement cartridge according to the first embodiment of the invention as seen from below.

As shown in FIGS. 1 to 3, a protective cap 2 is removably provided on a first end side of a cartridge main body 1 having a generally rectangular parallelepiped shape, the protective cap 2 protecting the first end side of the cartridge main body 1. A front surface of the cartridge main body 1 on the first end side is planar, and a puncture opening 3 is formed in a central portion of the planar surface.

At the back of the puncture opening 3, a puncture needle 4 is provided as shown in FIG. 2, and a puncture needle retainer 5 that retains the puncture needle 4 such that the puncture needle 4 is slidable toward the puncture opening 3 is provided. Note that the puncture needle retainer 5 is provided in a state in which a rear end thereof protrudes from the rear (rightward in FIG. 2) of the cartridge main body 1.

Furthermore, a sensor unit 6 is provided on an outer peripheral portion of the cartridge main body 1 on the first end side. The sensor unit 6 is constituted by a thin plate-shaped substrate 7, a spacer 8, and a cover 9 that are laminated together, and is integrated with the outer peripheral portion of the cartridge main body 1 on the first end side by bonding. Note that the substrate 7 extends from the first end side (front end) to a second end side (rear end) of the cartridge main body 1 in a longitudinal direction.

A depositing opening 10 on which blood is to be deposited is provided at a central portion of the front end of the sensor unit 6, and the depositing opening 10 is made to communicate with an introduction channel 11 in the sensor unit 6. Furthermore, at the back of the introduction channel 11, an introduction promoting hole 12 is provided which communicates with the introduction channel 11 and opens to the surface of the outer peripheral portion of the cartridge main body 1.

The introduction channel 11 is formed by sandwiching a slot cut into the spacer 8 from a front end thereof between the substrate 7 and the cover 9. At the back of the introduction channel 11, a reagent (not shown) is provided on the substrate 7, and blood drawn into the introduction channel 11 is allowed to react with the reagent. A connecting terminal 13 for electrically measuring this reaction is provided on the substrate 7, extending from the reagent portion to an end portion on the back side of the cartridge main body 1.

Note that the lengths of the spacer 8 and the cover 9 are set to about half the length of the substrate 7. Thus, the backward end portion of the connecting terminal 13, which is provided on the substrate 7, is exposed to the surface of the cartridge main body 1, as shown in FIG. 1.

The front surface of the cartridge main body 1 on the first end side is planar as described above, and in this front surface, a recessed portion 14 extending from one side end in a side surface to the other side end is provided between the puncture opening 3 and the depositing opening 10. The recessed portion 14 allows the puncture opening 3 for the puncture needle 4 and the depositing opening 10 of the sensor unit 6 to be spaced apart at a predetermined distance in a direction that is orthogonal to the longitudinal direction of the cartridge main body 1.

In this embodiment, the protective cap 2 has a bottomed tubular shape that is open on the side of the cartridge main body 1, and as shown in FIG. 3, a bottom portion 2a on one end side thereof is planar, and a cylindrical, puncture needle protector 15 is provided on a central portion of the planar surface. Thus, as shown in FIG. 2, the puncture needle 4 of the cartridge main body 1 is inserted into the puncture needle protector 15, and thereby the puncture needle 4 is protected.

Also, a flat plate-shaped protruding portion 16 is provided on a peripheral portion of the bottom portion 2a, the protruding portion 16 protruding from an inner side of the bottom portion 2a toward the second end side of the cartridge main body 1.

On a portion that is closer to the peripheral edge than the protruding portion 16 is a flat plate-shaped outer peripheral wall 17 is provided in a position at a predetermined distance from the protruding portion 16, the outer peripheral wall 17 protruding from the inner side of the bottom portion 2a toward the rear end of the cartridge main body 1. Note that the outer peripheral wall 17 protrudes beyond the protruding portion 16 toward the rear end of the cartridge main body 1.

An annular insertion receiving portion is formed by connecting the protruding portion 16 to the outer peripheral wall 17 at the bottom portion 2a side. The annular insertion receiving portion and the bottom portion 2a constitute a first sensor protector 16a having a bottomed tubular shape.

Furthermore, the protruding length of the outer peripheral wall 17, which constitutes the first sensor protector 16a, from the bottom portion 2a is set to be greater than the distance from the depositing opening 10 at the front end of the sensor unit 6 to the introduction promoting hole 12. A planar portion is formed on a surface of the outer peripheral wall 17 on the protruding side and on the side that faces the protruding portion 16, and this planar portion is used as a second sensor protector 16b.

The protective cap 2 having the first sensor protector 16a and the second sensor protector 16b is attached to the cartridge main body 1 by inserting the protruding portion 16 into the recessed portion 14 of the cartridge main body 1, as shown in FIG. 2.

In this state, the front end of the sensor unit 6 is inserted into the first sensor protector 16a having the bottomed tubular shape. The first sensor protector 16a closes the depositing opening 10 of the sensor unit 6 by the annular insertion receiving portion of the first sensor protector 16a covering the entire periphery of the front end of the sensor unit 6 in a sealing state.

Furthermore, the introduction promoting hole 12 of the sensor unit 6 abuts against the second sensor protector 16b. The second sensor protector 16b closes the introduction promoting hole 12 of the sensor unit 6 by the planar portion of the second sensor protector 16b covering the thin plate-shaped sensor unit 6 in close contact therewith.

That is to say, the first sensor protector 16a and the second sensor protector 16b of the protective cap 2 cover and close the depositing opening 10 and the introduction promoting hole 12, respectively, of the sensor unit 6. With this configuration, the introduction channel 11 communicating with the depositing opening 10 and the introduction promoting hole 12 are sealed, so that exposure of the reagent (not shown) disposed in the introduction channel 11 can be prevented.

Furthermore, every cartridge main body 1 according to this embodiment is provided with an individual protective cap 2, and therefore even when a plurality of biological information measurement cartridges are stored in a storage container, no biological information measurement cartridge will be exposed. As a result, whichever biological information measurement cartridge is used, proper measurement can be made every time.

Note that a rectangular guide wall 20 having protrusions and recesses is formed at a central portion on each side of the cartridge main body 1, the guide wall 20 extending from a middle portion to the rear end in the longitudinal direction. The guide walls 20 individually constitute portions where a user touches when handling the cartridge main body 1.

Hereinafter, a measurement with a biological information measurement cartridge according to this embodiment will be described taking a case where a nurse, who can be a user, measures blood glucose level of a patient in an examination room of a hospital as an example.

Figure 4:
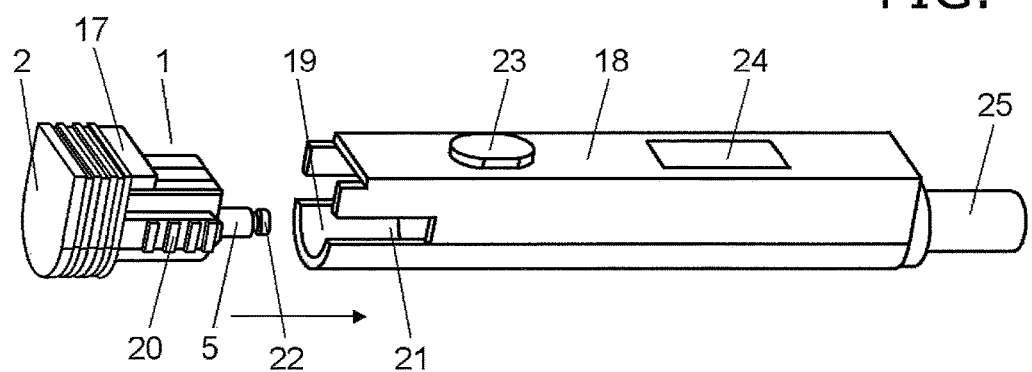
FIG. 4 is a perspective view of the biological information measurement cartridge and a measurement device according to the first embodiment of the invention.

First, as shown in FIG. 4, the nurse attaches the cartridge main body 1 with the protective cap 2 attached thereto to a device casing 18 of a measurement device for measuring biological information. More specifically, the cartridge main body 1 is inserted into an attachment port 19 of the device casing 18 from the puncture needle retainer 5 side of the cartridge main body 1. Note that the device casing 18 has an elongated pen-like shape as can be seen from FIG. 4, and is therefore shaped to be easy to grip with one hand.

A guide slot 21 is formed in a central portion on each side of the device casing 18 on the attachment port 19 side, the guide slot 21 extending backward from the attachment port 19. The cartridge main body 1 is attached to the device casing 18 with its guide walls 20 guided by the respective guide slots 21.

Figure 5:
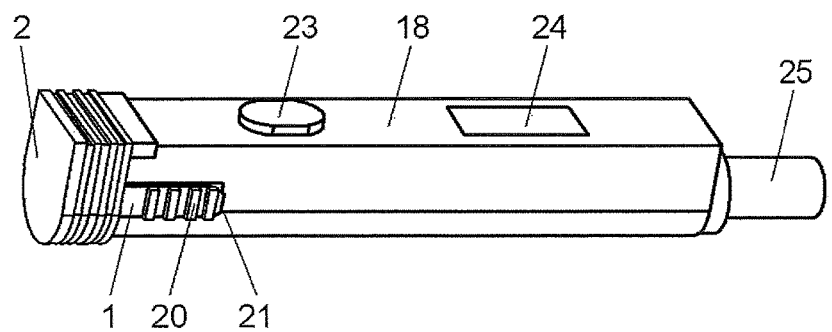
FIG. 5 is a perspective view of the biological information measurement cartridge and the measurement device according to the first embodiment of the invention.

When the guide walls 20 have been guided to the back of the guide slots 21, an attachment portion 22 provided at the rear end of the puncture needle retainer 5 is retained by an attachment portion retainer 101 in the device casing 18, and thus the attachment of the cartridge main body 1 to the device casing 18 is completed as shown in FIG. 5.

In this state, the connecting terminal 13 of the cartridge main body 1 is mechanically and electrically connected to a connecting pin (not shown) in the device casing 18.

Next, the nurse as a user holds a central portion of the device casing 18 with the right hand, for example, and, in this state, the nurse pinches an outer peripheral portion of the protective cap 2 with the left hand and extracts the protective cap 2 from the cartridge main body 1. At this time, since the attachment portion 22 of the cartridge main body 1 is retained by the attachment portion retainer 101 of the device casing 18, the cartridge main body 1 is not pulled out of the device casing 18.

Figure 6:
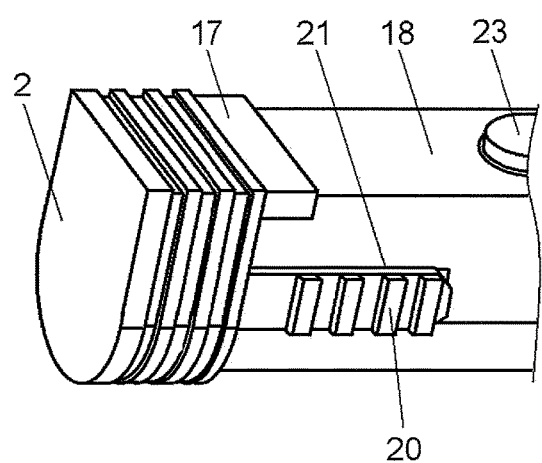
FIG. 6 is an enlarged perspective view of a relevant part of the biological information measurement cartridge and the measurement device according to the first embodiment of the invention.

Moreover, as shown in FIG. 6, the guide walls 20 are designed to protrude to the outside of the device casing 18 from the respective guide slots 21 of the device casing 18. Thus, the nurse can, for example, hold the central portion of the device casing 18 with the right hand and press the guide walls 20 on the attachment port 19 side with the thumb and the forefinger. As a result, the cartridge main body 1 can be stabilized in a state in which it is attached to the device casing 18.

Consequently, the protective cap 2 can be easily extracted from the cartridge main body 1.

Also, at this time, since the protrusions and recesses for slip prevention are formed in outer surfaces of the guide walls 20 and a circumferential surface of the tubular protective cap 2, the protective cap 2 can be easily extracted from the cartridge main body 1.

Figure 7:
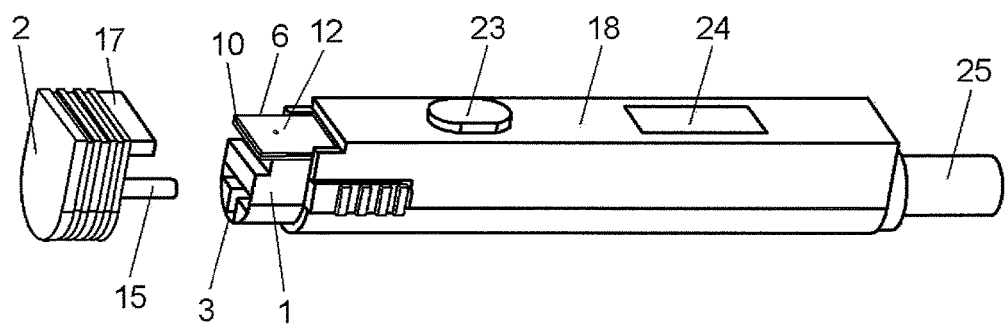
FIG. 7 is a perspective view of the biological information measurement cartridge and the measurement device according to the first embodiment of the invention.

FIG. 7 shows a state in which the protective cap 2 has been removed from the cartridge main body 1.

In this state, the puncture needle protector 15 of the protective cap 2 has been removed from the puncture needle 4, and the puncture needle 4 is exposed within the cartridge main body 1 (in this state, the puncture needle 4 does not protrude forward yet).

Moreover, in the sensor unit 6, the first sensor protector 16a has been removed from the depositing opening 10, the second sensor protector 16b has been removed from the introduction promoting hole 12, and thus the depositing opening 10 and the introduction promoting hole 12 are open.

As described above, since the first sensor protector 16a and the second sensor protector 16b cover and close the depositing opening 10 and the introduction promoting hole 12, respectively, of the sensor unit 6 until immediately before puncture, exposure of the reagent can be prevented.

Consequently, according to this embodiment, proper measurement can be made every time.

When the puncture needle 4 is exposed within the cartridge main body 1, and the depositing opening 10 and the introduction promoting hole 12 are open, as described above, preparations for puncture are completed.

Figure 8:
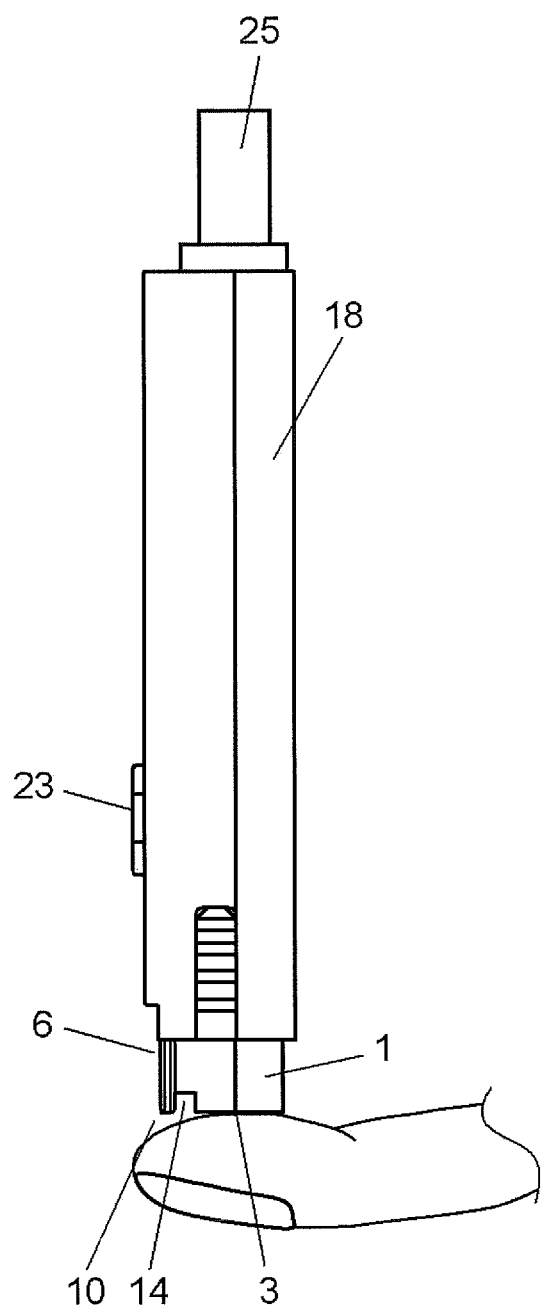
FIG. 8 is a side view of the biological information measurement cartridge and the measurement device according to the first embodiment of the invention during usage.

During puncture, the nurse holds the elongated pen-shaped device casing 18 of the measurement device with the right hand, for example, as if he/she holds a pen, and touches the forefinger, for example, to a puncture button 23 that is provided on an outer peripheral portion of the device casing 18. Then, as shown in FIG. 8, the nurse brings the puncture opening 3 of the cartridge main body 1 attached to the device casing 18 into contact with the ball of a finger of the patient, for example.

At this time, as described above, since the front surface of the cartridge main body 1 on the first end side is made planar, and the puncture opening 3 is provided in the central portion of the planar surface, this planar surface enables the puncture opening 3 to be in stable contact with the ball of the finger of the patient.

In this contact state, when the nurse presses the puncture button 23 with the forefinger, a driver 102 provided in the device casing 18 slides the puncture needle retainer 5 shown in FIG. 2 toward the puncture opening 3. Then, the puncture needle 4 protrudes from the puncture opening 3, and thus puncture is performed.

Note that, after this puncture operation is ended, the puncture needle 4 immediately retracts to the state shown in FIG. 2, and this puncture needle 4 does not come into contact with the finger again.

The nurse removes the puncture opening 3 from the punctured finger, and squeezes an area around the punctured portion of the punctured finger to cause an amount of blood that is necessary for detection to flow from the finger.

Figure 9:
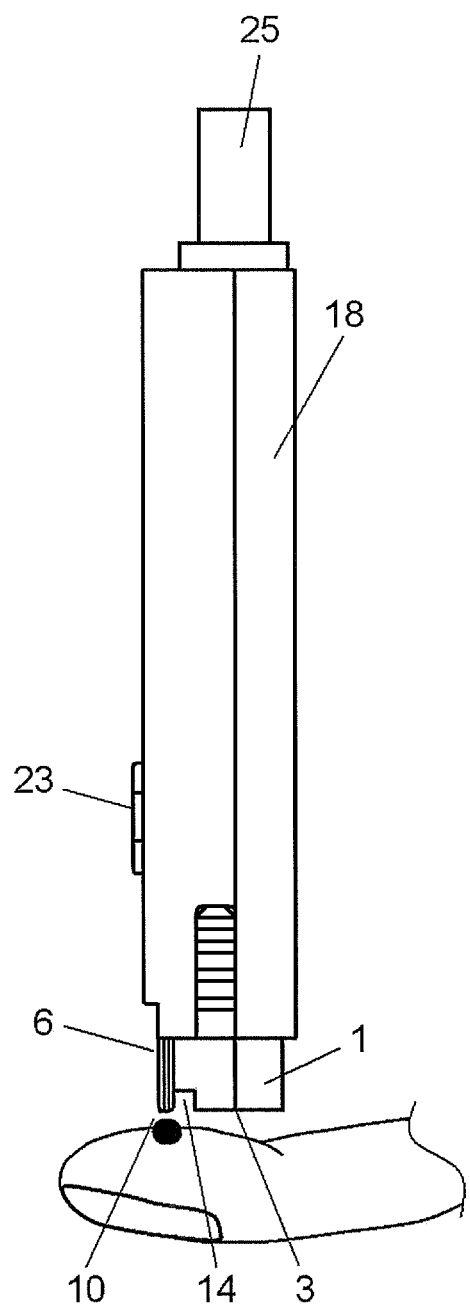
FIG. 9 is a side view of the biological information measurement cartridge and the measurement device according to the first embodiment of the invention during usage.

Then, as shown in FIG. 9, the blood is deposited on the depositing opening 10 of the sensor unit 6.

At this time, according to this embodiment, the puncture opening 3 and the depositing opening 10 are spaced apart at a predetermined distance by the recessed portion 14, as described above. Thus, while the blood is deposited on the depositing opening 10 of the sensor unit 6, the blood is prevented from being erroneously made to adhere to the puncture opening 3.

Accordingly, the blood can be properly deposited on the depositing opening 10. Thus, the biological information measurement cartridge of this embodiment is convenient.

The blood deposited on the depositing opening 10 is drawn into the back of the introduction channel 11 by capillary action in the introduction promoting hole 12 and then reacts with the reagent (not shown).

Since the cover 9 in FIG. 2 is composed of a transparent member, the blood that is drawn into the back of the introduction channel 11 can be observed through the cover 9 at this time.

Note that the reaction of the blood with the reagent (not shown) is transmitted to a measuring portion (not shown) in the device casing 18 via the connecting terminal 13 and the connecting pin (not shown). The blood glucose level measured by this measuring portion (not shown) is displayed in a display portion 24 shown in FIGS. 5 and 7, and the measurement is ended.

Finally, when the nurse as a user presses a discharge button 25 provided at an end portion of the device casing 18 on the back side, the attachment portion 22 in FIG. 2 is released from the attachment portion retainer 101, and the cartridge main body 1 is discharged to the outside of the device casing 18.

That is to say, since the cartridge main body 1 of this embodiment is integrally provided with the puncture needle 4 and the sensor unit 6, during preparation for measurement, the puncture needle 4 and the sensor unit 6 can be attached at a time by simply attaching the cartridge main body 1 to the device casing 18.

Moreover, at the end of the measurement, the puncture needle 4 and the sensor unit 6 can be discarded at a time by simply pressing the discharge button 25.

Accordingly, in the light of busy hospital services, the biological information measurement cartridge of this embodiment is very convenient.

Furthermore, with the cartridge main body 1 of this embodiment, since the puncture needle 4 and the sensor unit 6 can be discarded at a time, a new puncture needle 4 and a new sensor unit 6 of a new cartridge main body 1 are used to measure the blood glucose level of the next patient. Therefore, use of the same puncture needle 4 for a plurality of patients does not occur, and the risk of blood infection in the hospital services can be reduced.

In other words, according to this embodiment, since a new biological information measurement cartridge is used in which exposure of the sensor unit 6 is prevented until immediately before puncture, the risk of blood infection in the hospital services can be reduced, and furthermore, the cartridge main body 1 can be attached and discarded in an extremely simple manner. Thus, the biological information measurement cartridge of this embodiment is convenient.

Second Embodiment

Figure 10:
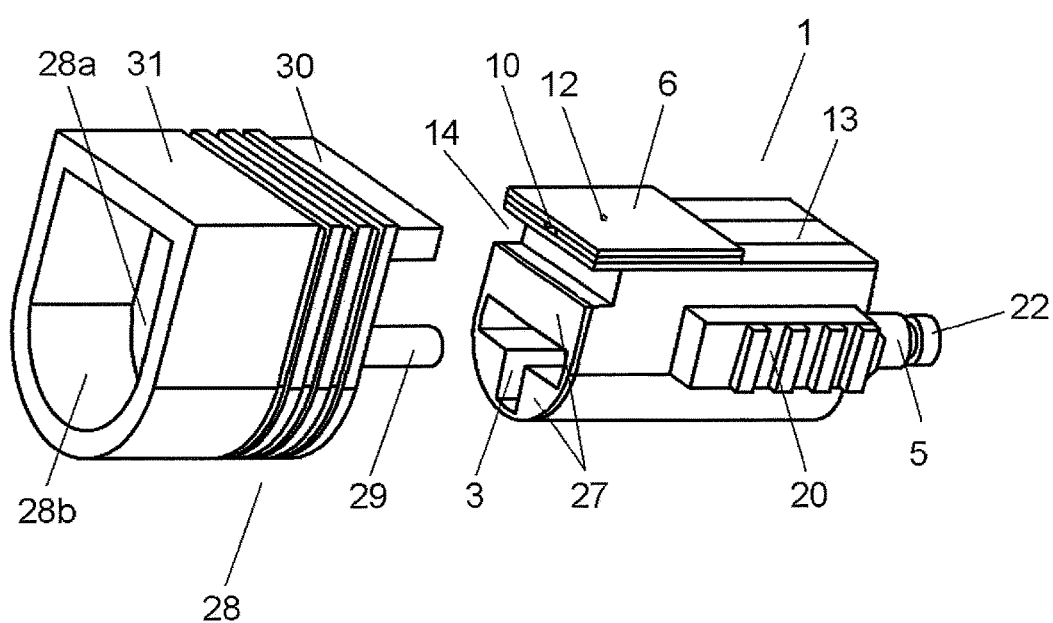
FIG. 10 is an exploded perspective view of a biological information measurement cartridge according to a second embodiment of the invention.

FIG. 10 shows a biological information measurement cartridge according to a second embodiment of the invention.

In the biological information measurement cartridge of the first embodiment, the protectors (the puncture needle protector 15, the first sensor protector 16a, and the second sensor protector 16b) provided in the protective cap 2 are provided on the same side with respect to the bottom portion 2a.

According to the second embodiment of the invention, as shown in FIGS. 10 to 13, in a protective cap 28, a cartridge cover portion 31 is provided on the side that is opposite to the side of the protectors (the puncture needle protector 29, the first sensor protector 32a, and the second sensor protector 32b) with respect to a bottom portion 28a.

Specifically, blood deposited on the sensor unit 6 can be concealed by putting the cartridge cover portion 31 on the front end side of the cartridge main body 1 after measurement, and thus the hygiene conditions can be improved.

A detailed description will be given below.

The cartridge cover portion 31 of the protective cap 28 is constituted by the bottom portion 28a and an annular wall 28b that is provided so as to protrude from a peripheral portion of the bottom portion 28a, and has a bottomed tubular shape that is open on the side opposite to the bottom portion 28a. The opening of the cartridge cover portion 31 has substantially the same shape as the outer peripheral shape of the cartridge main body 1 on the front end side and is open wide. The protruding length of the annular wall 28b of the cartridge cover portion 31 from the bottom portion 28a is set to be greater than the distance from the front end side of the sensor unit 6 to the introduction promoting hole 12.

In this manner, the cartridge cover portion 31 is provided on the side that is opposite to the side of protectors (a puncture needle protector 29, a first sensor protector 32a, and a second sensor protector 32b) with respect to the bottom portion 28a. Furthermore, the shape of the cartridge cover portion 31 is made significantly different from that of the side of those protectors.

The method according to which this cartridge cover portion 31 is used will be described using FIGS. 11 to 13.

First, a nurse, who can be a user, attaches the cartridge main body 1 with the protective cap 28 attached thereto to the device casing 18 in the same manner as in the case described in the first embodiment. After that, the protective cap 28 is removed from the cartridge main body 1, and puncture, depositing, and measurement are performed sequentially.

When the measurement is ended, the nurse attaches the removed protective cap 28 to the cartridge main body 1 again, but the nurse puts the cartridge cover portion 31 side, instead of the protector side, of the protective cap 28 on the cartridge main body 1.

Figure 11:
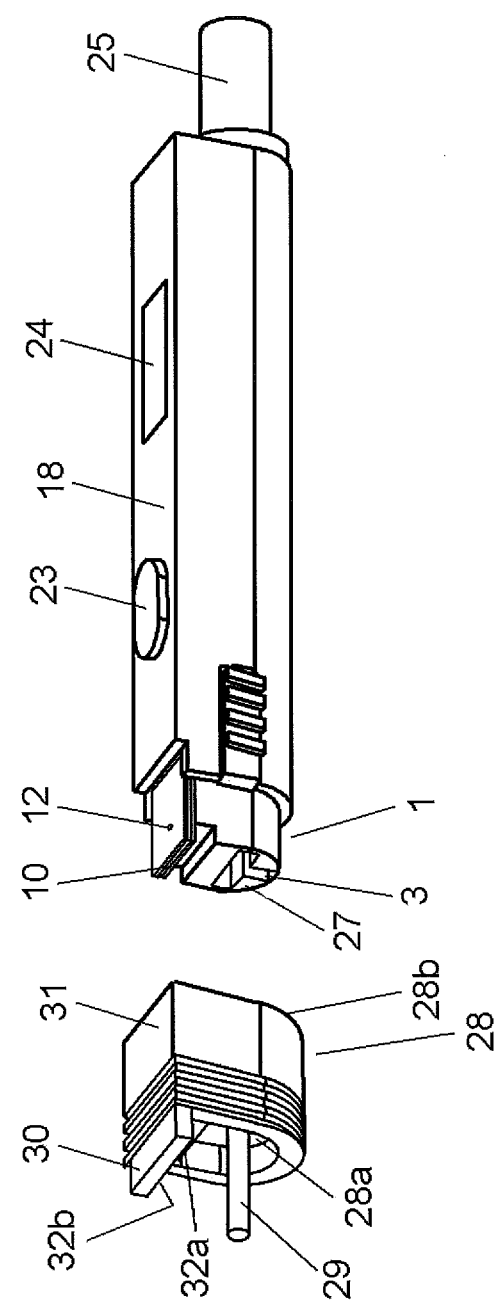
FIG. 11 is a perspective view of the biological information measurement cartridge and a measurement device according to the second embodiment of the invention.

More specifically, as shown in FIG. 11, the nurse first orients the cartridge cover portion 31 so that the cartridge cover portion 31 faces the front end side of the cartridge main body 1. At this time, as described above, since the shape of the cartridge cover portion 31 side located on the outer side of the bottom portion 28a is significantly different from that of the side of the protectors, the nurse can easily recognize the cartridge cover portion 31.

Figure 12:
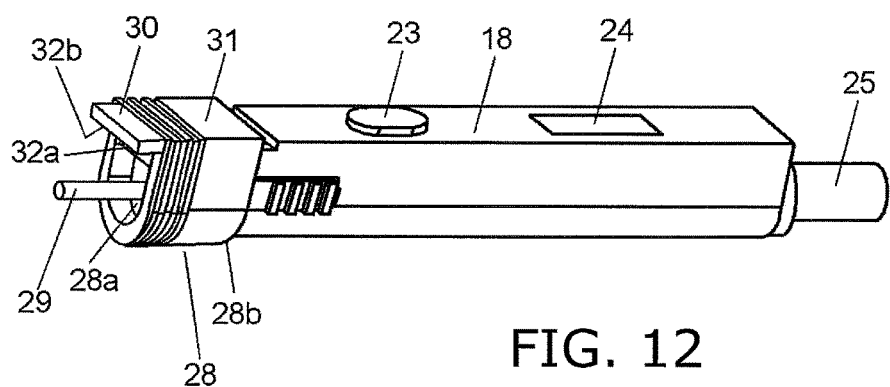
FIG. 12 is a perspective view of the biological information measurement cartridge and the measurement device according to the second embodiment of the invention.

Next, as shown in FIG. 12, the nurse puts the cartridge cover portion 31 on the front end side of the cartridge main body 1, thereby concealing the front end side of the cartridge main body 1.

At this time, as described above, since the protruding length of the annular wall 28b of the cartridge cover portion 31 from the bottom portion 28a is set to be greater than the distance from the front end side of the sensor unit 6 to the introduction promoting hole 12 the cartridge cover portion 31 can conceal the depositing opening 10, the introduction channel 11, and the introduction promoting hole 12 of the sensor unit 6.

Figure 13:
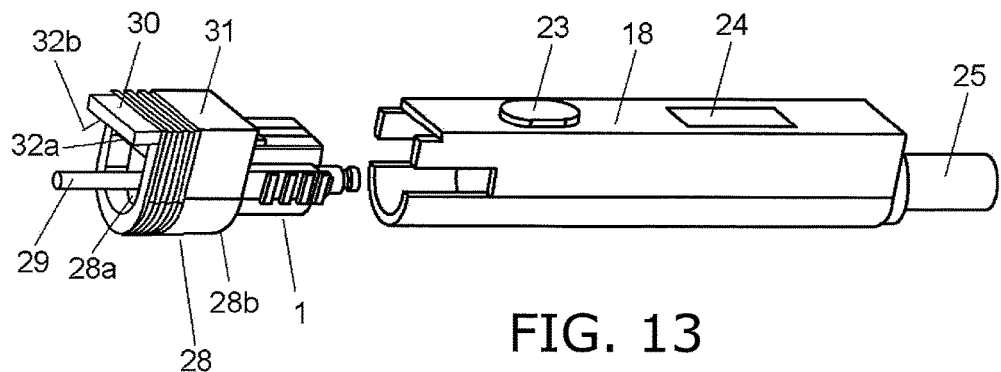
FIG. 13 is a perspective view of the biological information measurement cartridge and the measurement device according to the second embodiment of the invention.
Figure 14:
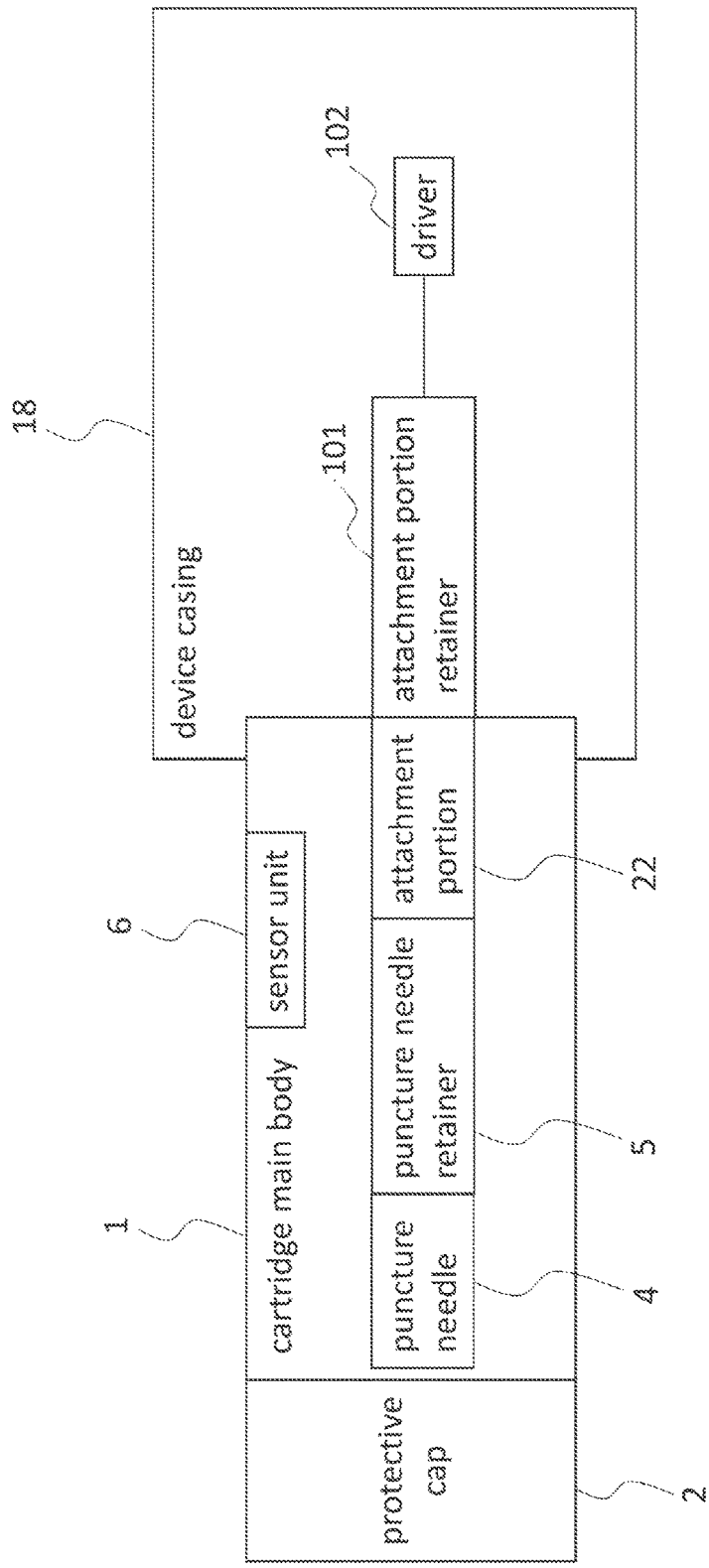
FIG. 14 is a block diagram showing configurations of a measurement device, a cartridge main body, and a protective cap.

After that, as shown in FIG. 13, when the nurse presses the discharge button 25 of the device casing 18, the cartridge main body 1 is discharged to the outside of the device casing 18 with the protective cap 2 put on the cartridge main body 1.

In this manner, at the end of the measurement, the cartridge main body 1 and the protective cap 28 in the integrated state can be discarded at a time by simply pressing the discharge button 25, and therefore, in the light of busy hospital services, the biological information measurement cartridge of this embodiment is very convenient.

When the cartridge main body 1 and the protective cap 28 are discarded, the cartridge cover portion 31 conceals the depositing opening 10 and the introduction promoting hole 12 of the sensor unit 6, thereby concealing the blood deposited on the sensor unit 6.

Consequently, the hygiene conditions can be improved.

Moreover, as described above, since the cover 9 of the sensor unit 6 is composed of a transparent member so that blood drawn into the introduction channel 11 during measurement can be observed, the blood in the introduction channel 11 is still visible after the measurement. In contrast, according to this embodiment, the cartridge cover portion 31 conceals even the introduction channel 11. Thus, the blood in the introduction channel 11 is not seen by other people and consequently can be prevented from making other people feel unpleasant.

Furthermore, in a state in which the cartridge cover portion 31 of the protective cap 28 is put on the cartridge main body 1, as described above, the shape of the cartridge cover portion 31 is made significantly different from that of the side of the protectors (the puncture needle protector 29, the first sensor protector 32a, and the second sensor protector 32b), and the puncture needle protector 29 is in a state in which it protrudes from the protective cap 28 as shown in FIGS. 11 to 13. Therefore, the nurse can recognize that this cartridge main body 1 is already used.

Furthermore, according to this embodiment, as shown in FIG. 10, a wiping portion 27 for wiping off the blood is provided in an area around the puncture opening 3 on the first end side of the cartridge main body 1. This wiping portion 27 is formed by, for example, producing a porous member such as filter paper in conformity with the peripheral shape of the puncture opening 3 and bonding this filter paper to the first end side of the cartridge main body 1.

Accordingly, the nurse can wipe off excess blood of a patient with the wiping portion 27 after measurement, and thus the biological information measurement cartridge of this embodiment is convenient.

Then, after the excess blood is wiped off, when the nurse puts the cartridge cover portion 31 of the protective cap 28 on the cartridge main body 1 as shown in FIG. 12, the cartridge cover portion 31 conceals the wiping portion 27. This can prevent making other people feel unpleasant and also improve the hygiene conditions.

Note that when putting the cartridge cover portion 31 on the cartridge main body 1, it is sufficient if the blood in the sensor unit 6 and the excess blood on the wiping portion 27 can be hidden. Thus, as described above, the cartridge cover portion 31 simply has the shape of a deep tube that is open wide. Accordingly, the nurse can easily put the cartridge cover portion 31 on the cartridge main body 1.

As described above, a biological information measurement cartridge according to the invention includes a cartridge main body having a rectangular parallelepiped shape and having a puncture opening on a first end side thereof and a protective cap removably attached to the first end side of the cartridge main body. The cartridge main body has a puncture needle provided at the back of the puncture opening, a puncture needle retainer retaining the puncture needle such that the puncture needle is slidable toward the puncture opening, and a sensor unit having a depositing opening on the first end side of the cartridge main body. The sensor unit has an introduction channel communicating with the depositing opening and an introduction promoting hole that communicates with the introduction channel and opens to the surface of the cartridge main body. Furthermore, the protective cap is provided with a puncture needle protector that covers the puncture needle, a first sensor protector that covers a depositing opening of the sensor unit, and a second sensor protector that covers the introduction promoting hole. With the above configuration, the invention enables prevention of exposure of the sensor unit.

In other words, the biological information measurement cartridge according to the invention includes the cartridge main body and the protective cap attached to the first end side of the cartridge main body. When the protective cap is attached to the cartridge main body, the first and second sensor protectors provided in the protective cap cover and close the depositing opening and the introduction promoting hole, respectively, of the sensor unit of the cartridge main body. Thus, exposure of the sensor unit can be prevented.

That is to say, since all of the biological information measurement cartridges according to the invention that are stored in a storage container are provided with individual protective caps, not only a biological information measurement cartridge to be used this time but also the other biological information measurement cartridges in the storage container are not exposed, and thus proper measurement can be made every time.

INDUSTRIAL APPLICABILITY

The invention is expected to be widely used as a biological information measurement cartridge and a measurement device using the biological information measurement cartridge.

The invention claimed is:
1. A biological information measurement cartridge comprising:
a cartridge main body including a first end side, a second end side, and a surface;
a sensor unit provided on the first end side of the cartridge main body; and
a protective cap removably provided on the first end side of the cartridge main body;
the cartridge main body including:
a puncture opening including a back, and being disposed on the first end side of the cartridge main body;
a puncture needle provided at the back of the puncture opening; and
a puncture needle retainer configured to retain the puncture needle such that the puncture needle is slidable toward the puncture opening;
the sensor unit including:
a depositing opening disposed on the first end side of the cartridge main body;
an introduction channel configured to communicate with the depositing opening; and
an introduction promoting hole configured to communicate with the introduction channel and open at a part of a surface of the sensor unit; and
the protective cap including:
a puncture needle protector in which the puncture needle of the cartridge main body is to be inserted; and
a sensor protector configured to close the depositing opening and the introduction promoting hole in a sealed state by contacting the sensor unit;
wherein:
a recessed portion is defined between the puncture needle and the sensor unit on the first end side of the cartridge main body;
the puncture needle and the sensor unit are spaced apart at a predetermined distance by the recessed portion in a direction that is orthogonal to a longitudinal direction of the cartridge main body;

the sensor protector includes a first bottom portion, an outer peripheral wall, an annular insertion receiving portion, and a protruding portion configured to be inserted into the recessed portion;

the outer peripheral wall includes a first bottom portion side and protrudes toward the second end side of the cartridge main body;

the annular insertion receiving portion is defined by connecting two side surfaces of the protruding portion to the first bottom portion side of the outer peripheral wall; and the protruding portion protrudes toward the second end side of the cartridge main body and has a flat plate shape.

2. The biological information measurement cartridge according to claim 1, wherein:

a protruding length of the outer peripheral wall is greater than a distance from the depositing opening to the introduction promoting hole.

3. The biological information measurement cartridge according to claim 2, wherein:

the outer peripheral wall includes a planar portion;

the planar portion is disposed on a first surface of the outer peripheral wall; and the first surface of the outer peripheral wall is disposed on a leading side of the outer peripheral wall, extends in a protruding direction, and faces the protruding portion.

4. The biological information measurement cartridge according to claim 1, further comprising:

a cartridge cover portion configured to cover the first end side of the cartridge main body, the cartridge cover portion provided on a first side of the protective cap that is opposite to a second side of the protective cap with the sensor protector.

5. The biological information measurement cartridge according to claim 4, wherein:

the cartridge cover portion includes a second bottom portion provided on the first side of the protective cap, and an annular wall provided on a peripheral portion of the second bottom portion.

6. The biological information measurement cartridge according to claim 5, wherein:

a shape of the first side of the protective cap is different from a shape of the second side of the protective cap.

7. The biological information measurement cartridge according to claim 1, further comprising:

a wiper configured to wipe off a biological sample provided in an outer peripheral portion of the puncture opening on the first end side of the cartridge main body.

8. A measurement device for measuring biological information, the measurement device comprising:

the biological information measurement cartridge according to claim 1;

a device casing including an attachment port, the attachment port being disposed on one end side of the device casing, and the cartridge main body being attached to the attachment port;

an attachment portion retainer provided at a back of the attachment port, and to which the puncture needle retainer is attached;

a driver configured to slide the puncture needle retainer toward the puncture opening; and a discharge button configured to discharge the cartridge main body from the device casing.

9. The measurement device according to claim 8, wherein:

the device casing further includes a guide slot disposed in a side surface; and the guide slot is configured to guide attachment of the cartridge main body from the attachment port toward a back side of the device casing.

10. The measurement device according to claim 9, further comprising:

a guide wall provided on a side surface of the cartridge main body;

wherein, when the guide wall of the cartridge main body is inserted in the guide slot, the guide wall protrudes from the guide slot to an outside of the device casing.

* * * * *